(12) United States Patent
Qiu

(10) Patent No.: US 12,138,451 B2
(45) Date of Patent: Nov. 12, 2024

(54) ADAPTIVE TRANSDERMAL IONTOPHORETIC INTRODUCTION SYSTEM FOR BEAUTY FIELD

(71) Applicant: Shanghai Jingxun Infotech Co., Ltd., Shanghai (CN)

(72) Inventor: Huaxuan Qiu, Shanghai (CN)

(73) Assignee: SHANGHAI JINGXUN INFOTECH CO., LTD., Shanghai (CN)

( * ) Notice: Subject to any disclaimer, the term of this patent is extended or adjusted under 35 U.S.C. 154(b) by 828 days.

(21) Appl. No.: 17/055,229

(22) PCT Filed: Jul. 12, 2019

(86) PCT No.: PCT/CN2019/095882
§ 371 (c)(1),
(2) Date: Nov. 13, 2020

(87) PCT Pub. No.: WO2019/219097
PCT Pub. Date: Nov. 21, 2019

(65) Prior Publication Data
US 2021/0121690 A1    Apr. 29, 2021

(30) Foreign Application Priority Data
May 16, 2018    (CN) .......................... 201810466993.X

(51) Int. Cl.
*A61N 1/32* (2006.01)
*A61N 1/04* (2006.01)
(Continued)

(52) U.S. Cl.
CPC .............. *A61N 1/328* (2013.01); *A61N 1/04* (2013.01); *A61N 1/303* (2013.01); *A61N 1/36* (2013.01)

(58) Field of Classification Search
CPC .......... A61N 1/328; A61N 1/04; A61N 1/303; A61N 1/36; A61N 1/0428; A61N 1/325; A61N 1/30
See application file for complete search history.

(56) References Cited

U.S. PATENT DOCUMENTS

| 2003/0097118 A1 | 5/2003 | Zhang et al. |
| 2005/0010146 A1* | 1/2005 | Levanon ............. A61F 13/0226 602/1 |

(Continued)

FOREIGN PATENT DOCUMENTS

| CN | 103826696 A | 5/2014 |
| CN | 204182020 U | 3/2015 |

(Continued)

OTHER PUBLICATIONS

Int'l Search Report issued Sep. 30, 2019 in Int'l Application No. PCT/CN2019/095882.

*Primary Examiner* — Robert J Utama
*Assistant Examiner* — Hamza A Darb
(74) *Attorney, Agent, or Firm* — Panitch Schwarze Belisario & Nadel LLP

(57) ABSTRACT

An adaptive transdermal iontophoretic introduction system for the beauty field is provided. Specifically, the system includes an iontophoretic introduction system, and a control and drive electronic system. The control and drive electronic system includes an operation system, a central processing system, an electrode drive system, a sensing system and a data communication system. The adaptive transdermal iontophoretic introduction system provides personalized transdermal drug delivery according to the actual condition of a user's skin, optimizes the dose, depth and speed of the transdermal drug delivery in real time, and maximizes the product usage effect and safety.

7 Claims, 2 Drawing Sheets

(51) Int. Cl.
*A61N 1/30* (2006.01)
*A61N 1/36* (2006.01)

(56) References Cited

U.S. PATENT DOCUMENTS

2014/0046240 A1* 2/2014 Anand .................... A61N 1/30
                                                   604/20
2016/0310049 A1* 10/2016 Rowe ................ A61B 5/14517

FOREIGN PATENT DOCUMENTS

| CN | 104918653 A | 9/2015 |
| CN | 106659889 A | 5/2017 |
| CN | 108853720 A | 11/2018 |
| WO | 2017213442 A1 | 12/2017 |

* cited by examiner

ADAPTIVE TRANSDERMAL IONTOPHORETIC INTRODUCTION SYSTEM FOR BEAUTY FIELD

CROSS-REFERENCE TO RELATED APPLICATIONS

This application is a Section 371 of International Application No. PCT/CN2019/095882, filed Jul. 12, 2019, which was published in the Chinese language on Nov. 21, 2019, under International Publication No. WO 2019/219097 A1, which claims priority under 35 U.S.C. § 119(b) to Chinese Application No. 201810466993, filed May 16, 2018, the disclosures of each of which are incorporated herein by reference in their entireties.

TECHNICAL FIELD

The present invention relates to cosmetology field, in particular to an adaptive transdermal iontophoretic introduction system.

BACKGROUND

Love for beauty is common to all people. Especially for women, beauty is their lifelong pursuit. With the improvement of economic level year by year, more and more women pay more attention to their appearance. Among them, skin care, as an important part for beauty, occupies most of women's consumption for beauty. Skin care has become a science in modern times.

With increasing pursuit for health and rapid development of dermatology, medical skin care products with higher safety and more effectiveness have become an unstoppable trend. It is also an inevitable trend to apply transdermal iontophoresis technology to the field of beauty.

A main purpose of the traditional transdermal iontophoresis technology is to deliver drugs into blood through skin. Therefore, in the traditional transdermal application mode, the skin is only a barrier that must be passed through. In view of this understanding, control mechanism of the traditional transdermal drug delivery technology is mainly focused on fixing drug delivery current at a predetermined strength (determined by clinical trials) that can safely repulse drug molecules across the skin barrier. A feedback system comprised in the control system is also designed to achieve and maintain a constant drug delivery current intensity.

At present, all skin beauty systems that have initially introduced the transdermal drug delivery technology still maintain traditional application thinking mode. In the field of beauty, the skin is no longer just a barrier; it is both a barrier and a final destination (dermis) that some drugs or cosmetic molecules are delivered to. As skin condition is improved due to the entry of the drugs or cosmetic molecules, the controlled body (skin) in the control system of the transdermal drug delivery will also change. Therefore, the constant current intensity of drug delivery will not be able to maximize beauty effect.

In summary, there is an urgent need in the field to develop an adaptive transdermal iontophoresis introduction system providing personalized transdermal drug delivery according to the actual skin condition of a user, with optimized dosage, depth, and speed of transdermal drug delivery in real time, so as to maximize product use effect and safety.

SUMMARY OF THE INVENTION

The purpose of the present invention is to develop an adaptive transdermal iontophoresis introduction system providing personalized transdermal drug delivery according to the actual skin condition of a user, with optimized dosage, depth, and speed of transdermal drug delivery in real time, so as to maximize product use effect and safety.

The present invention provides an adaptive transdermal iontophoresis introduction system in beauty field, wherein the system comprises:

an electroosmotic iontophoresis system: wherein the iontophoresis system is in contact with skin, and repulses an active agent to the skin layer through action of current or voltage outputting by an electrode driving system, thus realizing a purpose of transdermal iontophoresis into the skin;

a control and drive electronic system, wherein the control and drive electronic system comprises:

an operating system: wherein the operating system comprises a power supply; and/or a power switch; and/or a mode selection button;

a central processing system: wherein the central processing system dynamically calculates and adjusts an output electrode driving waveform based on at least one basic parameter, at least one feedback signal of a sensing system and optional auxiliary data, then provides it to the electrode driving system;

the electrode driving system: wherein the electrode driving system generates a driving current or voltage according to the output value of the central processing system; and the sensing system: wherein the sensing system can sense conditions of the contacted skin and feed back to the central processing system.

In another preferred embodiment, the control and drive electronic system further comprises a data communication system; wherein the data communication system has functions of receiving the basic parameters and auxiliary data, operating control, updating system, and uploading usage data.

In another preferred embodiment, the adjustment range of the dynamically calculates and adjusts an output electrode driving waveform is 0% to 500% of the basic parameter value.

In another preferred embodiment, the adjustment range of the dynamically calculates and adjusts an output electrode driving waveform is 50% to 500% of the basic parameter value.

In another preferred embodiment, the basic parameter on which the calculation of the central processing system is based and the adjustable electrode driving waveform comprises one or more characteristics of the following:

(i) transdermal delivery period;
(ii) maximum value of output current or voltage;
(iii) minimum value of output current or voltage;
(iv) period;
(v) duty cycle.

In another preferred embodiment, the auxiliary data comprises one or more characteristics selected from the following group:

(i) beauty ingredient;
(ii) dosage;
(iii) user's skin condition.

In another preferred embodiment, the user's skin condition is the skin condition before using the introduction system, and provides feedforward data for the calculation of the central processing system.

In another preferred embodiment, the user's skin condition is facial skin condition, comprising the forehead area, the nose area, the left cheek area, the right cheek area, the chin area, or a combination thereof.

In another preferred embodiment, the central processing system further comprises a memory device or an integrator to record an outputting total charge.

In another preferred embodiment, the electrode driving waveform is alternating current, and the memory device or integrator is used to keep the output charge in balance even when the system dynamically adjusts the current intensity.

In another preferred embodiment, the electrode driving waveform is direct current.

In another preferred embodiment, the electrode driving system is a current driving system.

In another preferred embodiment, the current driving system further comprises a current feedback circuit to keep the output current at an intensity set by the central processing unit when the skin resistance changes during the transdermal delivery time.

In another preferred embodiment, the electrode driving system comprises one or more current driving components.

In another preferred embodiment, the electroosmotic iontophoresis system comprises one or more pairs of electrode components.

In another preferred embodiment, each of the electrode components comprises a corresponding skin contact layer; wherein the contact layer is used to store the active agent containing medium and fluidly communicate with the electrode.

In another preferred embodiment, the active agent is one or more components selected from the following: hyaluronic acid, tranexamic acid, amino acids, peptides, collagen, vitamin C, vitamin B, and growth factor (EGF).

In another preferred embodiment, the electroosmotic iontophoresis system and the control and drive electronic system are two separate modules.

In another preferred embodiment, the electroosmotic iontophoresis system is a disposable electronic facial mask.

In another preferred embodiment, the electronic facial mask is conformable to the outer surface of the face.

In another preferred embodiment, the electroosmotic iontophoresis system further comprises some or all of the sensors in the sensing system.

In another preferred embodiment, the sensing system comprises a skin sensor; and/or a signal conditioning circuit; and/or an analog-to-digital converter.

In another preferred embodiment, the skin sensor comprises at least one sensor of the following: a skin moisture test sensor, a pH sensor, a sebum measurement sensor, a temperature sensor, and a biological resistance analysis sensor.

In another preferred embodiment, the data communication system comprises at least one interface of the following: near field communication, radio frequency communication, Wi-Fi, Bluetooth, ZigBee, GSM, CDMA, LTE, USB and RS232.

In another preferred embodiment, the data communication system is Bluetooth, which mainly communicates with the mobile phone APP.

In another preferred embodiment, input of the data communication system comprises one or more parameters or data of the following:
(i) transdermal delivery period;
(ii) maximum value of output current or voltage;
(iii) minimum value of output current or voltage;
(iv) period;
(v) duty cycle;
(vi) beauty ingredient;
(vii) dosage;
(viii) user data.

In another preferred embodiment, the input of the data communication further comprises an activation command.

In another preferred embodiment, the usage data output by the data communication comprises one or more parameters or data of the following:
(i) actual transdermal delivery period;
(ii) actual output current or voltage waveform or characteristics of the electrode driving system;
(iii) actual output charge of the electrode driving system;
(iv) user skin analysis based on the sensing system before using;
(v) user skin analysis based on the sensing system after using.

In another preferred embodiment, the mode selection buttons comprise: a high intensity mode button, a medium intensity mode button, and a low intensity mode button.

In another preferred embodiment, the power supply is a portable removable power supply.

The beneficial effect of the present invention is that the adaptive transdermal iontophoresis introduction system can provide personalized transdermal drug delivery according to the user's skin condition and dynamically adjust the drug delivery driving waveform and its parameters, so as to maximize the beauty effect and safety.

It should be understood that within the scope of the present invention, the above-mentioned technical features of the present invention and the technical features specifically described in the following (such as the embodiments) can be combined with each other to form a new or preferred technical solution. Due to space limitations, it will not be repeated here.

DETAILED DESCRIPTION

Figure 1:
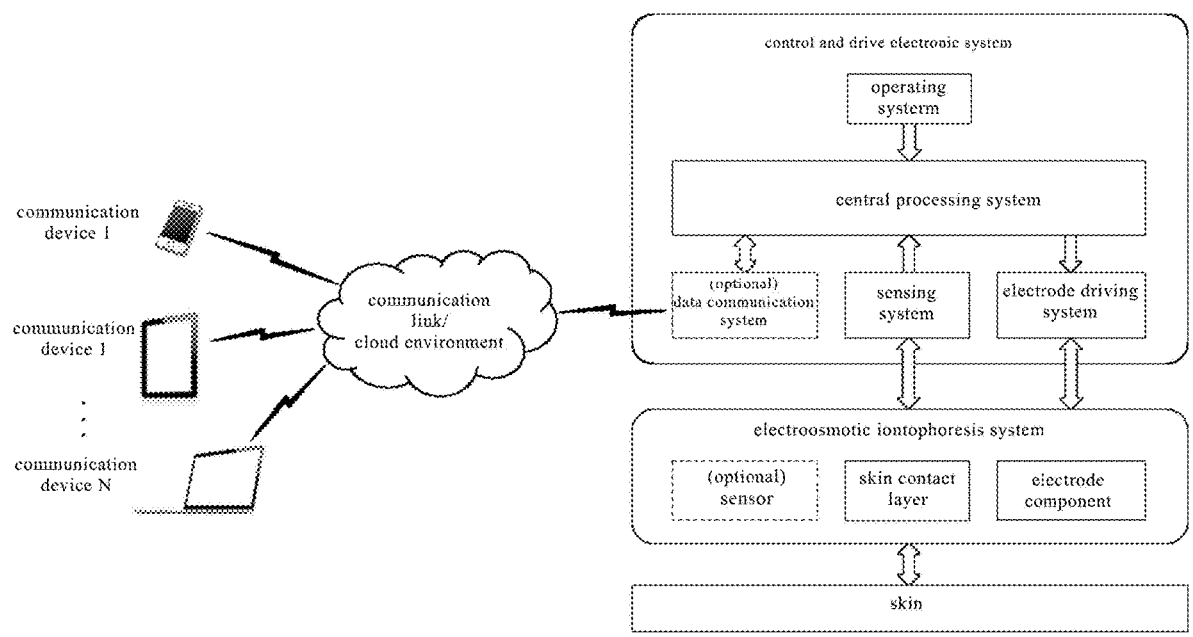
FIG. 1 is a schematic diagram of an adaptive transdermal iontophoresis introduction system of the present invention.

After extensive and in-depth research, the present inventors have developed an adaptive transdermal iontophoresis introduction system for the field of beauty for the first time. The system provides personalized transdermal drug delivery according to the users' skin conditions, and optimizes the dosage, depth, and speed of transdermal drug delivery in real time. The present invention has been completed on this basis.

An Adaptive Transdermal Iontophoresis Introduction System in Beauty Field

An adaptive transdermal iontophoresis introduction system in beauty field comprises: an electroosmotic iontophoresis system and a control and drive electronic system.

Wherein, the iontophoresis system is in contact with skin, repulses an active agent to the skin layer by action of current or voltage output by an electrode driving system, and then realizes a purpose of transdermal iontophoresis into the skin. The control and drive electronic system comprises an operating system, a central processing system, an electrode driving system, and a sensing system. Typically, the control and drive electronic system may further comprises a data communication system.

The operating system comprises a power supply, and/or a power switch, and/or a mode selection button. Through the power switch and the mode selection button, the user can choose to execute a drug delivery program with basic parameters and other auxiliary data.
Central processing system During the execution period of the drug delivery program, the central processing system dynamically adjusts and optimizes the output electrode driving waveforms based on at least one basic parameter in accordance with the feedback signal of the sensing system and optional auxiliary data to maximize the beauty effect of the product. Wherein, the main purpose of the auxiliary data is to provide feedforward data to the central processing unit for pre-optimization and generation of the electrode driving waveforms suitable for the user's transdermal drug delivery. The traditional transdermal drug delivery technology stops here, while the adaptive system of the present invention continues to dynamically adjust and optimize the electrode driving waveform of the user's transdermal drug delivery based on the feedback signal during the drug delivery period.

The auxiliary data may comprise beauty ingredient, dosage, user data, and so on. Among them, the user data may include the user's skin condition (such as body resistance), age, gender, and so on. The user's skin condition is the skin condition before using the introduction system, and provides feedforward data for the calculation of the central processing system. In a facial beauty application, the user's skin condition is a facial skin condition, selected from: the forehead area, the nose area, the left cheek area, the right cheek area, the chin area, and a combination thereof.

The basic parameters of the electrode driving waveform may comprise the transdermal delivery period, the maximum of output current or voltage. In one or more preferred embodiments, the electrode driving waveform is alternating current, the basic parameters of which may further comprise minimum of output current or voltage value (may be negative), period, duty cycle and other parameters. The adjustment range of the output electrode driving waveform is limited to 0% to 500% of its basic parameter value, preferably 50% to 200%, to achieve flexibility to adapt to various users' skin conditions while maintaining a high level of safety standard.

Figure 2A:
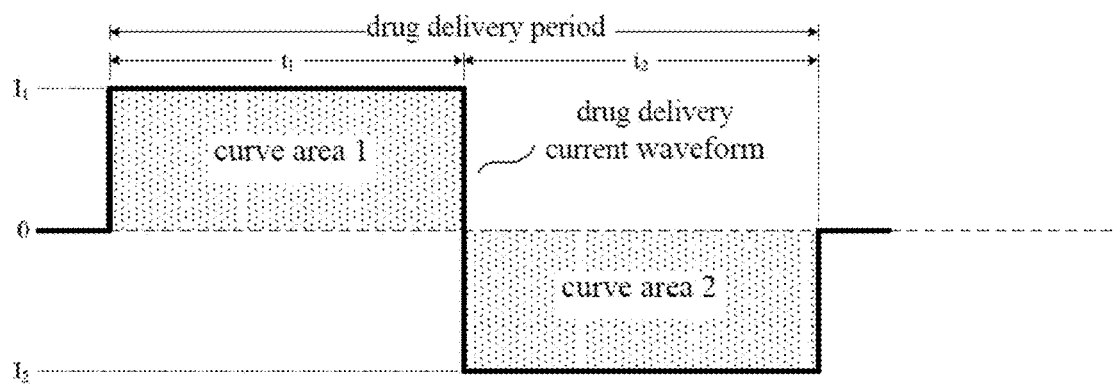
FIG. 2a is a schematic diagram of an AC electrode driving waveform of a traditional transdermal drug delivery system.

The explanation will be given below in combination with FIG. 2a, FIG. 2b and FIG. 2c. It should be noted that the description and figures only illustrate the principle of the present invention. Therefore, it can be appreciated that those skilled in the art can think out various arrangements that embody the principle of the present invention and are included in the spirit and scope thereof, even if these arrangements are not explicitly described or shown herein. The following description will use an alternating current as an example of the electrode driving waveform. For those skilled in the art, the same example is also applicable to direct current (just assume that the dosing waveform is the positive half period of the alternating current waveform). FIG. 2a is a schematic diagram of an AC electrode driving waveform of the traditional transdermal drug delivery system. The parameters $I_1$, $I_2$, $t_1$, and $t_2$ were generated based on feedforward data such as drugs and/or user information. Once the drug delivery program was started, the drug delivery driving waveform and its parameters may be constant in the entire drug delivery period.

Figure 2B:
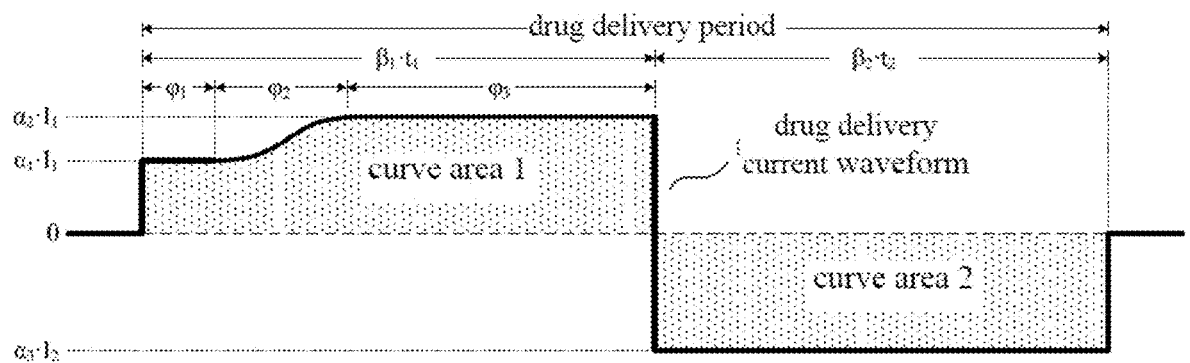
FIG. 2b is a schematic example in which the adaptive transdermal iontophoresis introduction system of the present invention provided personalized transdermal drug delivery according to the user's skin condition and dynamically adjusted the drug delivery driving current.

In the adaptive iontophoresis introduction system of the present invention, as shown in FIG. 2b, all parameters can be dynamically adjusted according to the actual users' conditions during the drug delivery period. Among them, $\alpha$ $\beta$ were adjustment ratios, and the ranges were 0 to 500% (preferably 50% to 200%). Assuming $\alpha_i<1$, and $\beta_i>1$, FIG. 2b shows an example in which the user's skin was too dry. At beginning of the drug delivery period, the central processing system found through the sensing system that the user's skin was too dry, and the dry skin is more susceptible to electrical burns. Therefore, the central processing system limited the drug delivery driving current during $\varphi_1$ period. During $\varphi_2$ period, the user's skin had been gradually improved by the beauty ingredient in the $\varphi_1$ period, and the tolerance to the current had been correspondingly improved, so the central processing system may gradually increase the intensity of the drug delivery current. During $\varphi_3$ period, the central processing system had increased the drug delivery current to the highest applicable intensity for the user. In order to optimize user experience and shorten use time, the drug delivery current was maintained at this highest applicable intensity during the remaining drug delivery period.

Figure 2C:
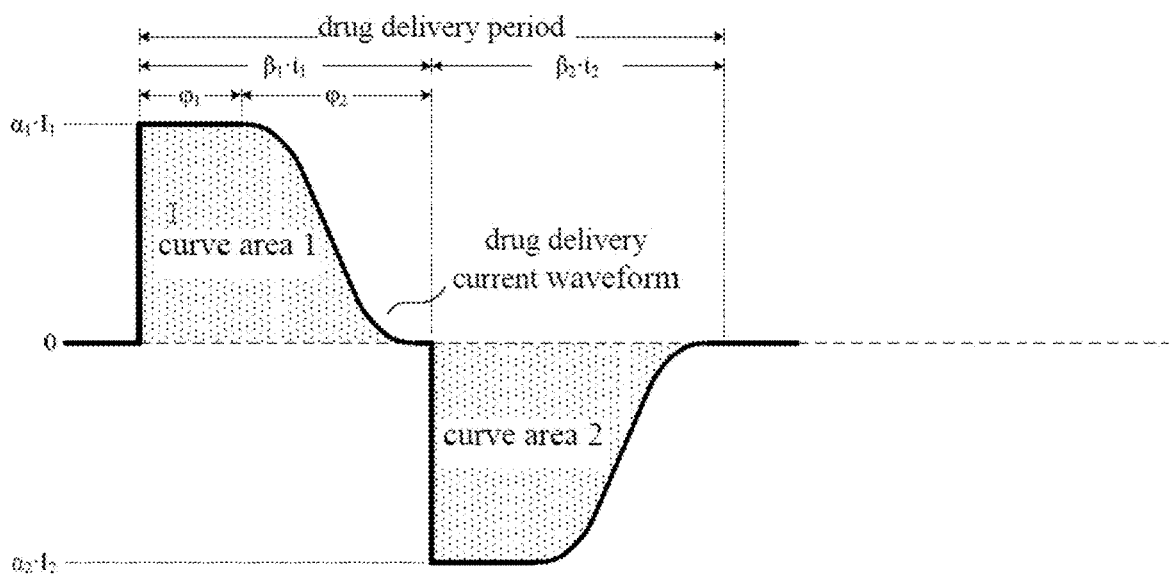
FIG. 2c is a schematic example in which the adaptive transdermal iontophoresis introduction system of the present invention provided personalized transdermal drug delivery according to the user's skin condition and dynamically adjusted the drug delivery driving current.

In FIG. 2c, $\alpha$, $\beta$ were also the adjustment ratios, and the ranges were 0 to 500% (preferably 50% to 200%). Assuming $\alpha_i>1$, $\beta_i<1$, FIG. 2c shows an example in which the user's skin is in good condition. At beginning of the drug delivery period, the central processing system found through the sensing system that the user's skin condition was very good, and its tolerance to the drug delivery driving current was also very high. Therefore, during $\varphi_1$ period, the drug delivery current exceeding the basic parameters was used. During $\varphi_2$ period, the central processing system sensed through the sensing system that concentration of the drugs and/or beauty ingredients in the skin had been saturated, which had reached the maximum value that can produce effective beauty effects. Therefore, the central processing system gradually reduced the intensity of the drug delivery current and ends treatment course early. Finally, it is worth noting that the above two examples based on FIGS. 2b and 2c are not necessarily for two different users or two different treatment courses. The same user may also receive different drug delivery driving current on different areas of the skin at the same time in one treatment course.

A main advantage of using alternating current waveforms is that they can keep the charge balance of the drug output current to avoid skin burns. The outputting total charge may be calculated by integrating the output current. In FIGS. 2a, 2b, and 2c, the amount of output charge in the positive and negative directions are marked as "curve area 1" and "curve area 2", respectively. In order to keep charge balance of the AC dosing current waveform, "curve area 1" and "curve area 2" in each of the above figures must be approximately equal. In the traditional transdermal drug delivery system, as shown in FIG. 2a, it is only necessary to ensure that the product of ($I_1$ and $t_1$) and ($I_2$ and $t_2$) are approximately equal for charge balance when generating the driving waveform for drug delivery before the drug delivery period is executed. In the adaptive iontophoresis introduction system of the present invention, the driving waveform and its parameters of drug delivery may be adjusted during operation. Therefore, in one or more preferred embodiments, the central processing system further comprises a memory device or an integrator to record the outputting total charge. As shown in FIG. 2b, the positive current and negative current can be different arbitrary waveforms, so an integrator must be used to ensure that "curve area 1" and "curve area 2" are roughly equal. In the embodiment of FIG. 2c, the current waveform of the positive half period may be recorded by the memory device, and copied and output in the opposite direction during the negative half period.

Electrode Driving System

The electrode driving system generates a driving current or voltage according to the output value of the central processing system.

In the present invention, the electrode driving waveform is alternating current. Typically, the electrode driving system is a current driving system.

The current driving system further comprises a current feedback circuit to maintain the output current at an intensity set by the central processing system when the skin resistance changes during the transdermal delivery time.

The electrode driving system comprises one or more current driving components. Taking facial beauty as an example, with the cooperation of multiple current driving components, multiple pairs of electrodes on different parts of the face can provide different dosing plans for different skin types in different areas.

Sensing System

The sensing system can sense the condition of the contacted skin and feed it back to the central processing system. The sensing system may comprise a skin sensor, and/or a signal conditioning circuit, and/or an analog-to-digital converter. Wherein, the skin sensor includes at least one sensor of the following: a skin moisture test sensor, a pH sensor, a sebum measurement sensor, a temperature sensor, and a biological resistance analysis sensor.

Electroosmosis Iontophoresis System

The iontophoresis system is in contact with the skin and repulses an active agent to the skin layer through action of current or voltage output by the electrode driving system, thus realizing the purpose of transdermal iontophoresis into the skin.

The electroosmotic iontophoresis system comprises one or more pairs of electrode components, and each electrode component comprises a corresponding skin contact layer. The contact layer is used to store the medium containing the active agent and fluidly communicate with the electrode. Wherein, the active agent comprises one or more ingredients of the following: hyaluronic acid, tranexamic acid, amino acids, peptides, collagen, vitamin C, vitamin B, growth factor (EGF) and a combination thereof.

Data Communication System

The control and drive electronic system further comprises a data communication system; wherein the data communication system has functions of receiving the basic parameters and auxiliary data, operating control, updating system, and uploading usage data. The data communication system comprises at least one interface of the following: near field communication, radio frequency communication, Wi-Fi, Bluetooth, ZigBee, GSM, CDMA, LTE, USB and RS232. In a preferred embodiment, as shown in FIG. 1, the control and drive electronic system can be connected to one or more communication devices and exchange data through the data communication system via a communication link or a cloud environment. Among them, examples of the communication devices comprise mobile computing devices, such as mobile phones, tablets, computers, and so on. In another preferred embodiment, the control and drive electronic system can be connected to and exchange data via the Internet or other cloud-based communication devices through the data communication system.

In the present invention, the data communication system mainly communicates with the mobile phone APP. Input of the data communication system comprises one or more parameters or data of the following: transdermal delivery period, maximum of output current or voltage, minimum of output current or voltage, period, duty cycle, beauty ingredient, dosage, user's skin condition, and so on. Wherein, the input of the data communication may further comprise an activation command to prevent the user from overusing or misusing the product.

The usage data output by the data communication system comprises one or more parameters or data of the following: the actual transdermal delivery period, the waveforms or characteristics of actual output current or voltage of the electrode driving system, actual output charge of the electrode driving system, user skin analysis based on the sensing system before using, user skin analysis based on the sensing system after using, etc. Through the data communication system to connect with the communication device, the user's skin condition is uploaded to the cloud, and the data is used to calculate and recommend the next time to use the product. Using products too frequently is wasteful and will not produce better cosmetic effects, while using products too little will not achieve the desired cosmetic effects.

Facial Mask

In one or more embodiments, the electroosmotic iontophoresis system and the control and drive electronic system of the present invention are two separate modules. Wherein, the electroosmotic iontophoresis system is a disposable electronic facial mask, and the electronic facial mask is conformable to the outer surface of the face; and the control and drive electronic system is a reusable beauty smart hardware.

The electronic facial mask in the present invention further comprises some or all of the sensors in the sensing system, especially the sensors that need to be in direct contact with the skin.

All documents mentioned in the present invention are cited as references in this application, as if each document was individually cited as a reference. In addition, it should be understood that after reading the above teaching content of the present invention, those skilled in the art can make various changes or modifications to the present invention, and these equivalent forms also fall within the scope defined by the appended claims of the present application.

What is claimed is:

1. An adaptive transdermal iontophoresis introduction system in a beauty field, wherein the system comprises:
   an electroosmotic iontophoresis system, wherein the iontophoresis system is in contact with skin, and repulses an active agent to a skin layer through action of current or voltage outputting by an electrode driving system, thus realizing a purpose of transdermal iontophoresis into the skin;
   a control and drive electronic system, wherein the control and drive electronic system comprises:
   an operating system, wherein the operating system comprises a power supply; a power switch; and a mode selection button;
   a central processing system, wherein the central processing system dynamically calculates and adjusts an output electrode driving waveform based on one or more basic parameter and, one or more feedback signal of a sensing system, then provides the output electrode driving waveform to the electrode driving system, wherein the electrode driving waveform is alternating current, and the central processing system comprises an integrator to integrate the alternating current waveform and record an outputting total charge;

the electrode driving system, wherein the electrode driving system generates a driving current or voltage according to the output value of the central processing system; and the sensing system, wherein the sensing system senses conditions of the contacted skin and feeds back to the central processing system in order to dynamically adjust and optimize the electrode driving waveform based on sensed conditions and feedback signals, and wherein the sensing system comprises a skin sensor, a signal conditioning circuit and an analog-to-digital converter, wherein the skin sensor comprises a skin moisture test sensor, a pH sensor, a sebum measurement sensor, a temperature sensor, and a biological resistance analysis sensor.

2. The system of claim 1, wherein the control and drive electronic system further comprises a data communication system; wherein the data communication system has functions of receiving the basic parameter and auxiliary data, operating control, updating system, and uploading usage data.

3. The system of claim 1, wherein the adjustment range of the dynamically calculates and adjusts the output electrode driving waveform is 0% to 500% of the basic parameter value.

4. The system of claim 1, wherein the basic parameter on which the calculation of the central processing system is based and the adjustable electrode driving waveform comprises one or more characteristics selected from the group consisting of:
 (i) transdermal delivery period;
 (ii) maximum value of output current or voltage;
 (iii) minimum value of output current or voltage;
 (iv) period; and
 (v) duty cycle.

5. The system of claim 1, wherein the central processing system dynamically calculates and adjusts the output electrode driving waveform based on one or more basic parameter, one or more feedback signal of the sensing system, and one or more auxiliary data, wherein the auxiliary data comprises one or more characteristics selected from the group consisting of:
 (i) beauty ingredient;
 (ii) dosage; and
 (iii) user's initial skin condition before using the system.

6. The system of claim 1, wherein the electrode driving system comprises one or more current driving components.

7. The system of claim 1, wherein the active agent is one or more components selected from the following: hyaluronic acid, tranexamic acid, amino acids, peptides, collagen, vitamin C, Vitamin B, and growth factor.

* * * * *